United States Patent
Choi et al.

(10) Patent No.: US 9,988,632 B2
(45) Date of Patent: Jun. 5, 2018

(54) COMPOSITION INCLUDING PINT GENE EXPRESSION INHIBITOR OR PINT ACTIVITY INHIBITOR AND USE THEREOF

(71) Applicant: Samsung Electronics Co., Ltd., Suwon-si, Gyeonggi-do (KR)

(72) Inventors: Hyojei Choi, Seongnam-si (KR); Myoungsoon Kim, Anyang-si (KR); Youngsam Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days. days.

(21) Appl. No.: 15/378,368

(22) Filed: Dec. 14, 2016

(65) Prior Publication Data

US 2017/0183656 A1   Jun. 29, 2017

(30) Foreign Application Priority Data

Dec. 24, 2015   (KR) .......................... 10-2015-0186781

(51) Int. Cl.
| | | |
|---|---|---|
| *C07H 21/02* | (2006.01) | |
| *C07H 21/04* | (2006.01) | |
| *C12N 15/113* | (2010.01) | |
| *A61K 8/60* | (2006.01) | |
| *A61Q 19/00* | (2006.01) | |
| *C12Q 1/68* | (2018.01) | |

(52) U.S. Cl.
CPC ............ *C12N 15/113* (2013.01); *A61K 8/606* (2013.01); *A61Q 19/00* (2013.01); *C12N 2310/14* (2013.01); *C12N 2320/30* (2013.01); *C12Q 1/6881* (2013.01); *C12Q 2600/178* (2013.01)

(58) Field of Classification Search
CPC .. C12N 15/113; C12N 2310/11; A61K 31/713
See application file for complete search history.

(56) References Cited

U.S. PATENT DOCUMENTS

| | | |
|---|---|---|
| 6,020,135 A | 2/2000 | Levine et al. |
| 6,171,798 B1 | 1/2001 | Levine et al. |
| 2016/0271163 A1 | 9/2016 | Marine et al. |

FOREIGN PATENT DOCUMENTS

WO   WO 2015/024986 A1   2/2015

OTHER PUBLICATIONS

Fan et al., BMC Genomics, 2015, 16:793.*
Marin-Bejar et al. (Genome Biology, 2013, 14, R104), Supplemental information only, pp. 1-22.*
Baker et al., "Clearance of p16Ink4a-positive senescent cells delays ageing-associated disorders", *Nature*, 479: 232-236 (2011).
Herbig et al., "Cellular Senescence in Aging Primates", *Science*, 311: 1257 (2006).
Marin-Bejar et al., "Pint lincRNA connects the p53 pathway with epigenetic silencing by the Polycomb repressive complex 2", *Genome Biology*, 14(9): 1-16 (2013).
Zhu et al., "The Achilles' heel of senescent cells: from transcriptome to senolytic drugs", *Aging Cell*, 14(4): 644-658 (2015).

* cited by examiner

*Primary Examiner* — Amy H Bowman
(74) *Attorney, Agent, or Firm* — Leydig, Voit & Mayer, Ltd.

(57) ABSTRACT

Provided are a composition for stimulating DNA damage in cells, the composition including a p53 induced non-coding transcript (PINT) gene expression inhibitor or a PINT activity inhibitor, a method of killing senescent cells in a subject, and a method of monitoring DNA damage in cells.

6 Claims, 5 Drawing Sheets

FIG. 4
(A) Comet Tail Moments
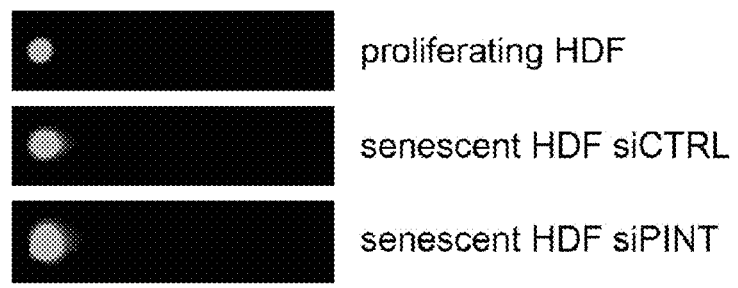
(B)
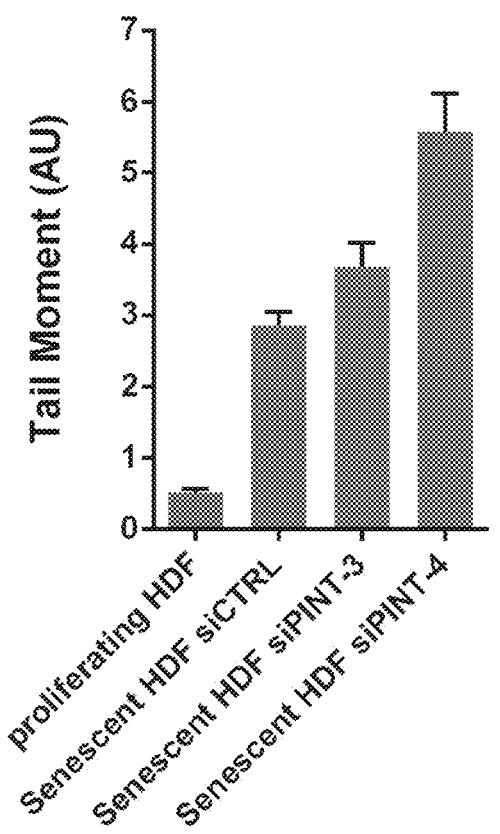

COMPOSITION INCLUDING PINT GENE EXPRESSION INHIBITOR OR PINT ACTIVITY INHIBITOR AND USE THEREOF

CROSS-REFERENCE TO RELATED APPLICATION

This application claims the benefit of Korean Patent Application No. 10-2015-0186781, filed on Dec. 24, 2015, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,363 Byte ASCII (Text) file named "726091_ST25.TXT", created on Dec. 14, 2016.

BACKGROUND

1. Field

The present disclosure relates to a composition including a p53-induced non-coding transcript (PINT) gene expression inhibitor or a PINT activity inhibitor, and use thereof.

2. Description of the Related Art p53-induced non-coding transcript (PINT) is a kind of intracellular lincRNA, and is known to bind with polycomb repressive complex 2 (PRC2) and regulate transcription. PINT expression is regulated by p53 protein in mouse cells. PINT exists as multiple isoforms.

The longest PINT isoform is known to contain four exons, which displayed a high level of expression in most tissues examined. PINT has three p53 binding sites: a promoter-proximal binding site and two distal binding sites positioned a few hundred thousand base pairs away from a transcriptional start site. Functional analysis revealed that p53 binds to these regulatory sites and mediates the activation of PINT following induction of p53.

Despite the above-described background, there is still a demand for a PINT inhibitor and a method of using the same.

SUMMARY

An aspect provides a composition for stimulating DNA damage in cells, the composition including one or more of a PINT expression inhibitor that inhibits PINT gene expression and a PINT activity inhibitor that inhibits PINT activity.

Another aspect provides a method of killing senescent cells in a subject, the method including administering to the subject one or more of the expression inhibitor inhibiting PINT gene expression and the activity inhibitor inhibiting PINT activity.

Still another aspect provides a method of monitoring DNA damage in cells, the method including measuring a PINT level in a cell-containing sample.

BRIEF DESCRIPTION OF THE DRAWINGS

These and/or other aspects will become apparent and more readily appreciated from the following description of the exemplary embodiments, taken in conjunction with the accompanying drawings in which:

FIG. 4 shows in panels (A) and (B) the results of comet assay of measuring DNA damage in siRNA-introduced young and senescent cells.

DETAILED DESCRIPTION

Figure 1:
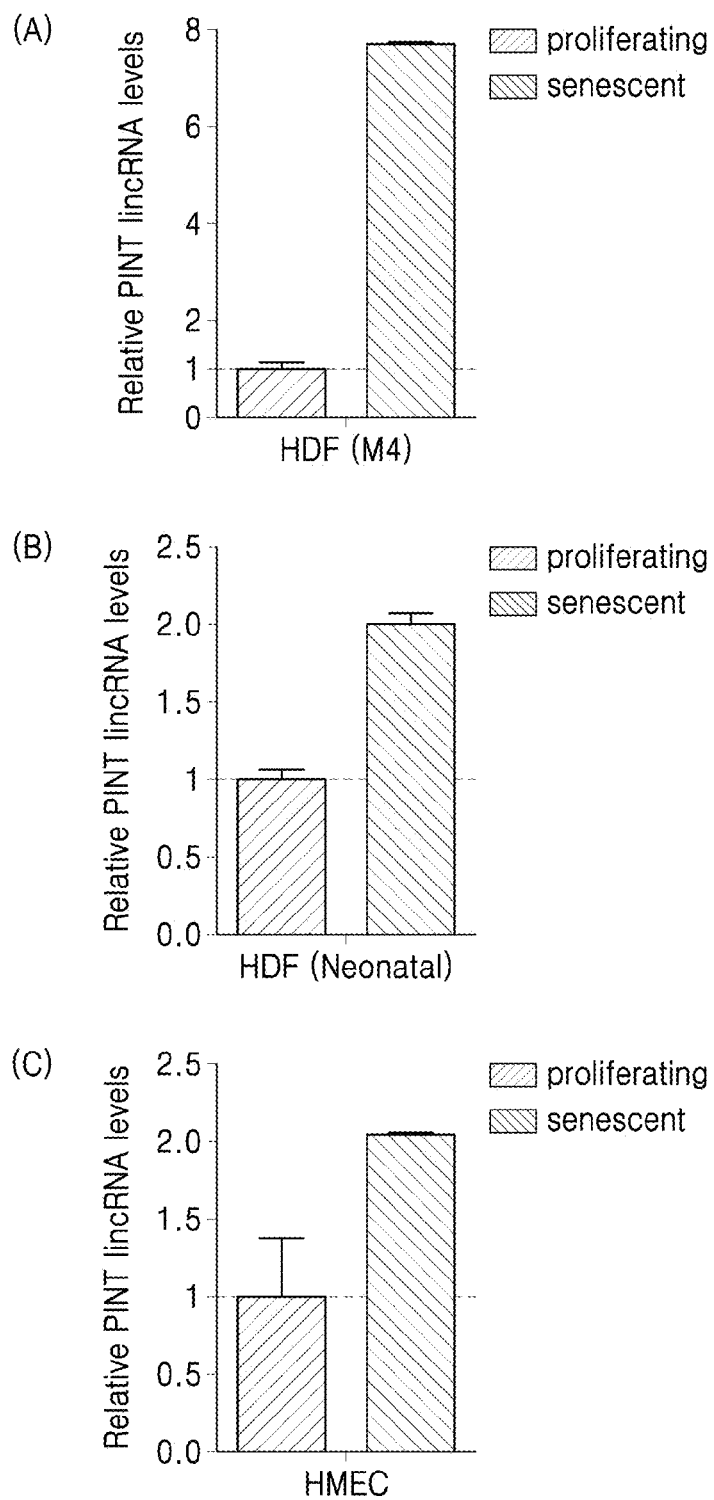
FIG. 1 shows PINT levels in young cells and senescent cells, wherein panel (A) pertains to HDF (M4) cells, panel (B) pertains to HDF (neonatal) cells, and panel (C) pertains to HMEC cells.

An aspect provides a composition for stimulating DNA damage in cells, the composition including one or more of an expression inhibitor inhibiting p53 induced non-coding transcript (PINT) gene expression and an activity inhibitor inhibiting PINT activity.

The PINT gene or PINT may be derived from a human. The PINT gene may exist on human chromosome 7q32.3. The PINT gene may have a nucleotide sequence described in NCBI accession no. 109851.1. The PINT gene may have a nucleotide sequence of SEQ ID NO: 1. The PINT is also called lincRNA (long non-coding RNA).

The PINT gene encodes PINT, which is an RNA molecule that can have any of ten isoforms present in human cells. The ten isoforms may have nucleotide sequences described in NCBI accession nos. NR_015431.2, NR_024153.2, NR_034120.1, NR_109850.1, NR_109852.1, NR_109853.1, NR_109854.1, NR_109855.1, NR_110472.1 and NR_110473.1, respectively. The ten isoforms have nucleotide sequences of SEQ ID NO: 2, 3, 4, 5, 6, 7, 8, 9, 10, and 11, respectively.

The PINT expression inhibitor or PINT activity inhibitor includes any inhibitor that inhibits PINT gene expression or PINT activity. The expression inhibitor or the activity inhibitor may be a nucleic acid molecule comprising a nucleotide sequence complementary to all or a part of the antisense or sense strand (or both) of the PINT gene or PINT. The nucleotide sequence may be RNA, DNA, or a hybrid thereof. The expression inhibitor or the activity inhibitor may be selected from the group consisting of small interfering RNA (siRNA), small hairpin RNA (shRNA), microRNA (miRNA), Piwi-interacting RNA (piRNA), small nuclear RNA (snRNA), and antisense oligonucleotide. The expression inhibitor or the activity inhibitor may be formulated to penetrate a cell membrane and/or a nuclear membrane, or may be included in a vehicle such as a vector. The vector may be a plasmid or a viral vector. The vehicle may include a nucleic acid construct to which the nucleotide sequence is linked. The expression inhibitor or the activity inhibitor may be non-naturally occurring, artificially created or prepared. The expression inhibitor or the activity inhibitor may be conjugated to another compound or moiety, for example, a cell membrane penetrating moiety or a material that enhances cell kill, such as a cytotoxic agent or radioactive material.

The siRNA may be selected from the group consisting of siRNAs that bind PINT. As used herein, siRNA may be a double stranded RNA molecule including 20 to 25, for example, 20 to 24, 20 to 23, 20 to 22, 21 to 25, or 22 to 25 base pairs in length. siRNA may play a role in the RNA interference pathway, which interferes with expression of specific genes with complementary nucleotide sequences. siRNA may cause an RNA transcript to be broken down. Examples of siRNAs targeting PINT include siRNAs each comprising a pair of nucleotide sequences of SEQ ID NO: 12 and SEQ ID NO: 13; SEQ ID NO: 14 and SEQ ID NO: 15; SEQ ID NO: 16 and SEQ ID NO: 17; SEQ ID NO: 18 and SEQ ID NO: 19; and SEQ ID NO: 20 and SEQ ID NO: 21.

The PINT expression inhibitor or the PINT activity inhibitor may stimulate cell death. The expression inhibitor or the activity inhibitor may induce DNA damage of cells. Thus, the PINT expression inhibitor or PINT activity inhibitor (or composition comprising same) may be used to stimulate cell death in senescent cells.

The composition may be used to specifically stimulate DNA damage and/or cell death of senescent cells in comparison with young cells. As used herein, the "senescence of a cell" or "cellular senescence" refers to a process that includes, as compared with a reference "young" cell, one or more of a decrease in cell proliferation ability or an increase in cell death rate, a decrease in autophagy activity, an accumulation of lipofuscin, an increase in β-galactosidase activity, an increase of mitochondria-derived reactive oxygen species, and a decrease in mitochondrial membrane potential, or to a process causing the phenomena above. Herein, the reference "young" cell may be a known non-senescent cell of the same type. Similarly, a "young cell" exhibits, as compared with a reference "senescent" cell, one or more of an increase in cell proliferation ability or a decrease in cell death rate, an increase in autophagy activity, a decrease in lipofuscin accumulation, a decrease in β-galactosidase activity, a decrease of mitochondria-derived reactive oxygen species, and an increase in mitochondrial membrane potential. Herein, the reference "senescent" cell may be a known senescent cell of the same type. A reference "young" cell may be a cell, for example, a skin cell, a fibroblast, a mammary epithelial cell, or a nerve cell derived from a person aged about 18 to about 25, about 18 to about 23, or about 18 to about 20 who are normal and healthy. The reference "young" cell also may be a cell that is passaged 10 times or less, has a doubling time of about 1 day or shorter, or has a combination thereof. A reference "senescent" cell may be a cell that has been passaged 30 times or more, has a doubling time of about 14 days or longer, or a combination thereof.

The composition may be administered to a subject or a site which shows symptoms of senescent cells (cellular senescence). The symptoms of senescent cells may be, for example, an increase in skin wrinkles, an increase in skin pigmentation, a decrease in skin elasticity, or a combination thereof, as compared with a control group. The control group may be any reference subject or site of a reference subject that is not exhibiting symptoms of cell senescence. The control group may be, for example, a person aged about 18 to about 25, about 18 to about 23, or about 18 to about 20 who are normal and healthy. The person may be a male or female. The composition may be topically administered to the senescent site. The senescent site may be a site on the skin which has more wrinkles, freckles, pigmentation spots, or a combination thereof, as compared with other sites. The senescent site may be determined by measuring a senescence marker in a tissue or cell, for example a skin fibroblast. The senescence marker may be, for instance, a reactive oxygen species (ROS), ki67 protein, p21 protein etc. Higher ROS levels indicate that the cell is more senescent, and lower levels of ki67 and p21 protein indicates that the cell is less senescent. The senescence marker also may be mitogenesis rate of a cell, a level of DNA damage etc. A lower mitogenesis rate indicates that the cell is more senescent, and a higher level of DNA damage indicates that the cell is more senescent.

The composition may be used in combination with one or more additional therapeutic agents to treat a disease associated with increased cellular senescence level.

In the composition, the cells may be cells of a mammal including a human. The mammal may have a disease associated with increased cellular senescence level. The cells may exist in vitro or in vivo.

The composition may further include a pharmaceutically acceptable carrier. With regard to the composition, the "pharmaceutically acceptable carrier" generally refers to an inert material, i.e., a material used in combination with an active ingredient to assist the application of the active ingredient. The carrier may include a pharmaceutically acceptable excipient, additive, or diluent generally used. The carrier may include one or more selected from, for example, a filler, a binder, a disintegrant, a buffer, a preservative, an antioxidant, a lubricant, a flavoring agent, a thickener, a coloring agent, an emulsifier, a suspending agent, a stabilizer, and an isotonic agent.

The composition may include the PINT expression inhibitor or the PINT activity inhibitor in a "therapeutically effective amount". In the composition, the "therapeutically effective amount" refers to an amount that is sufficient to cause a therapeutic effect when administered to a subject in need of treatment. The term "treatment" refers to a practice of treating a disease or a medical symptom, e.g., a disease associated with cellular senescence, in a subject, for example, a mammal including a human, and examples of the treatment are as follows: (a) prevention of the occurrence of a disease or a medical symptom, that is, prophylactic treatment of a patient; (b) alleviation of a disease or a medical symptom to any degree, that is, removal or recovery of a disease or a medical symptom in a patient; or (c) inhibition of a disease or a medical symptom, that is, delaying onset or stopping the progression a disease or a medical symptom in a subject. The "therapeutically effective amount" may be appropriately selected by one of ordinary skill in the art. The "therapeutically effective amount" may be, for example, about 0.01 mg to about 10,000 mg, about 0.1 mg to about 1000 mg, about 1 mg to about 100 mg, about 0.01 mg to about 1000 mg, about 0.01 mg to about 100 mg, about 0.01 mg to about 10 mg, or about 0.01 mg to about 1 mg.

The composition may be administered orally or parenterally (e.g., intravenous, intraperitoneal, or subcutaneous), rectally, or topically. Therefore, the composition may be formulated in various forms including tablets, capsules, aqueous solutions, or suspensions. In the case of tablet formulation for oral use, an excipient such as lactose or corn starch, and a lubricant such as magnesium stearate, may be generally added to the composition. In the case of capsule formulation for oral use, lactose and/or dry corn starch may be used as a diluent. When an aqueous suspension for oral use is required, an active ingredient may be used in combination with an emulsifier and/or a suspending agent. If necessary, a particular sweetening agent and/or a flavoring agent may be added. In the case of neural, intramuscular, intraperitoneal, subcutaneous, and intravenous administration, a sterile solution of an active ingredient is generally prepared, thereby appropriately adjusting and buffering the pH of the solution. In the case of intravenous administration, the total concentration of solutes is adjusted to render the formulation isotonicity. The composition may be prepared as an aqueous solution containing a pharmaceutically acceptable carrier having a pH of 7.4 as of salt water. The solution may be introduced into muscle or nerve blood flow of a patient by local bolus injection.

The composition may further include a DNA damage-inducing agent. DNA damage-inducing agents include, for example, etoposide, gemcitabine, cisplatin, carboplatin, oxaliplatin, camptothecin, 5-fluorouracil, temozolmide etc.

Another aspect provides a method of killing senescent cells in a subject by inhibiting PINT expression or PINT activity in the cells. The method can comprise, for instance, administering to a subject one or more of the PINT expression inhibitor or the PINT activity inhibitor, optionally as a pharmaceutical composition, particularly a topical composition. All features of the method pertaining to the PINT expression inhibitor, PINT activity inhibitor, formulation, therapeutically effective amount, and mode of administration are as previously described herein.

Without wishing to be bound by any particular theory or mechanism of action, it is believed that the method described herein may specifically stimulate DNA damage and/or cell death of senescent cells in comparison with young cells.

With regard to the method, those skilled in the art may appropriately select a route of administration depending on a patient's condition. The administration may be oral, parenteral, or topical administration. The administration may be topically applied to a tissue including senescent cells. The administration may be topically applied to skin tissue, muscle tissue, or nerve tissue.

With regard to the method, the "effective amount" may be an amount effective to treat symptoms associated with increased cellular senescence level in a mammal. The administration amount may vary, as described above, according to a variety of factors, such as a patient's condition, an administration route, or physician's determination. The effective administration amount may be estimated by a dose-response curve obtained in vitro or from an animal model test. The ratio or concentration of the compound of the present invention may be included in the composition to be administered according to chemical properties, the route of administration, or therapeutic amounts. The administration amount may be administered to a subject in an effective amount of about 1 μg/kg to about 1 g/kg per day, or about 0.1 mg/kg to about 500 mg/kg weight per day. The dose may vary depending on a subject's age, weight, susceptibility, or symptoms.

The method may further include administering a DNA damage-inducing agent to a subject. The DNA damage-inducing agent may be a DNA topoisomerase inhibitor, for example, etoposide. The DNA damage-inducing agent may be a DNA polymerase inhibitor, for example, aphidicolin.

With regard to the method, the subject may be a subject having a senescent tissue site. The administering may further include topical administration to the senescent tissue site. The senescent site may be a site on the skin which has wrinkles, freckles, pigmentation spots, or a combination thereof, for instance, a site that has many such features as compared with sites of the same or another person known to be non-senescent.

Still another aspect provides a method of monitoring DNA damage in cells, the method including measuring a PINT level in a cell-containing sample.

The measuring may include any measuring method or technique of a transcript PINT. The measuring may include nucleic acid amplification, southern blotting, sequencing, hybridization, or a combination thereof.

The method may further include separating the sample from a subject (e.g., biopsy).

The method may further include comparing the level with a PINT level measured in a control sample. The control sample may be a sample predetermined to include "young" (non-senescent) cells. The method may further include determining that the sample is senescent if the PINT level measured in the cell-containing sample is higher than the PINT level measured in the control sample.

The composition for stimulating DNA damage in cells according to an aspect may be used to stimulate DNA damage in cells.

The method of killing senescent cells in a subject according to another aspect may be used to efficiently kill senescent cells in the subject.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to Examples. However, these Examples are for illustrative purposes only, and the scope of the invention is not intended to be limited by these Examples.

EXAMPLE 1

1. PINT Levels in Different Cells

PINT lincRNA levels were measured in different young cells and senescent cells derived from humans.

In detail, the young cells were human dermal fibroblast (HDF) (hereinafter, referred to as 'HDF cell' or 'HDF (neonatal)') obtained from neonatal foreskin, human dermal fibroblast (HDF) M4 cell (hereinafter, referred to as 'HDF M4 cell' or 'HDF (M4)') obtained from the foreskin of a 4-year-old boy, and human mammary epithelial cell (HMEC) (hereinafter, referred to as 'HMEC cell' or 'HMEC') obtained from ATCC® PCS-600-010™. The young cells for the purposes of the experiments were cells of the above cell lines that were passaged 10 times or less and have a doubling time of about 1 day. The senescent cells were cells of the same cell lines that were passaged 33 to 50 times and have a doubling time of about 14 days or longer. The young cells and senescent cells were inoculated in 6-well plates at a density of 50,000 cells/well and 20,000 cells/well, respectively. The inoculated cells were cultured in 2 ml of a DMEM medium containing 10% (v/v) FBS, and 1× penicillin/streptomycin and high concentrations of glucose, glutamine, and pyruvate under conditions of 37° C. and 5% $CO_2$ for 3 days.

mRNAs were isolated from all the cells thus prepared, and then quantitative polymerase chain reaction (qPCR) was performed using nucleotide sequences of SEQ ID NOS: 22 and 23 as PINT primers to measure PINT levels.

FIG. 1 shows PINT levels in the young cells and the senescent cells. In FIG. 1, proliferating and senescent represent young cells and senescent cells, respectively. In FIG. 1, the vertical axis represents the PINT level of senescent cells relative to the PINT level of young cells, when the PINT level of young cells was taken as 1. As shown in FIG.

1, senescent cells of HDF(M4), HDF(neonatal), and HMEC showed relative PINT levels of 7.69, 2.00, and 2.04, which are remarkably higher than those of young cells. In FIG. 1, young cells of HDF(M4), HDF(neonatal), and HMEC were those passaged 8 times, 6 times, and 4 times, respectively and all had a doubling time of 1 day. Further, senescent cells of HDF(M4), HDF(neonatal), and HMEC were those passaged 33 times, 53 times, and 13 times, respectively and all had a doubling time of 14 days. Therefore, it is suggested that PINT imparts resistance to cells against stimulus or stress that causes cell death or apoptosis of senescent cells.

2. PINT Levels by DNA Damage in Cells

PINT lincRNA levels were measured according to DNA damage in cells. The cells were young cells HDF(M4) and HDF(neonatal) derived from humans, explained in section 1.

The young cells HDF(M4) and HDF(neonatal) used to induce DNA damage in cells were those passaged 8 times and 9 times, respectively and all had a doubling time of 1 day. Further, senescent cells HDF(M4) and HDF(neonatal) were those passaged 33 times and 49 times, respectively and all had a doubling time of 14 days. The cells thus prepared were cultured under the same conditions as in section 1 for 2 days, and further cultured for 24 hours, except that they were treated with 10 µM etoposide (Sigma-Aldrich) and 10 µM aphidicolin (Sigma-Aldrich) as DNA damage inducers. As a negative control, the cells were treated with dimethyl sulfoxide (DMSO) (Sigma-Aldrich). Thereafter, mRNAs were isolated from all the cells, and then quantitative polymerase chain reaction (qPCR) was performed using nucleotide sequences of SEQ ID NOS: 22 and 24 as PINT primers to measure PINT levels. Aphidicolin is a substance that inhibits eukaryotic DNA polymerases. Etoposide inhibits DNA topoisomerase II and induces cell cycle arrest in mid-phase to inhibit cell proliferation.

Figure 2:
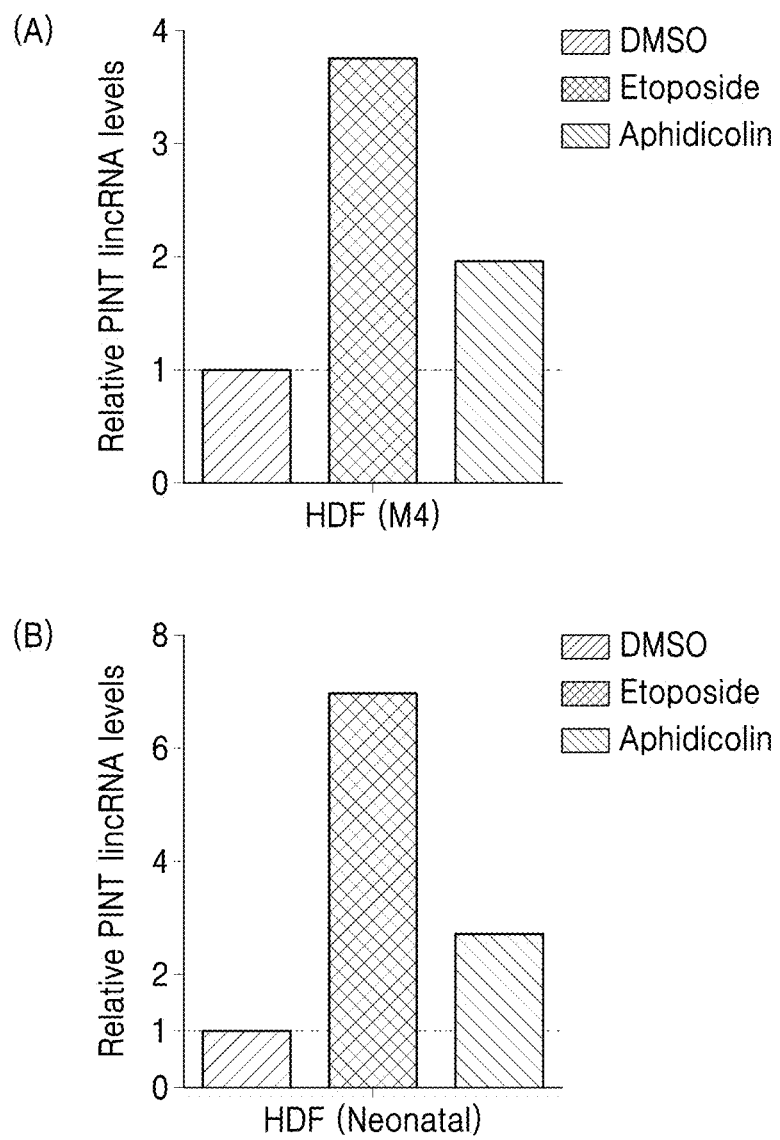
FIG. 2 shows PINT levels in young cells in the presence of DNA damage inducers, wherein panel (A) pertains to HDF (M4) cells, panel (B) pertains to HDF (neonatal) cells.

FIG. 2 shows PINT levels in young cells in the presence of DNA damage inducers. In FIG. 2, the vertical axis represents the PINT level of young cells in the presence of DNA damage inducers relative to the PINT level of young cells, where the PINT level of young cells in the absence of DNA damage inducers was taken as 1. As shown in FIG. 2, young cells of HDF(M4) and HDF(neonatal) showed remarkably increased relative PINT levels of 3.77 and 7.00 in the presence of etoposide and 1.95 and 2.72 in the presence of aphidicolin.

3. DNA Damage Increase of Senescent Cells by Inhibition of PINT Expression in Cells (3.1) Preparation of siRNA To inhibit PINT gene expression and/or PINT activity, the following 5 siRNAs including sequences complementary to PINT gene of SEQ ID NO: 1 were designed and synthesized (Cosmogenetech, Korea).

The siRNAs includes nucleotide sequences of SEQ ID NO: 12 and SEQ ID NO: 13; SEQ ID NO: 14 and SEQ ID NO: 15; SEQ ID NO: 16 and SEQ ID NO: 17; SEQ ID NO: 18 and SEQ ID NO: 19; and SEQ ID NO: 20 and SEQ ID NO: 21, respectively and hereinbelow, these siRNAs are called siPINT-1, siPINT-2, siPINT-3, siPINT-4, and siPINT-5, respectively.

It was examined whether the siRNAs decrease PINT levels in senescent cells. First, HDF(neonatal) young cells being passaged 9 times and having a doubling time of 1 day and HDF(neonatal) senescent cells being passaged 49 times and having a doubling time of 14 days, which were prepared in section 1, were transfected with 25 nM siRNA. The cells were cultured for 72 hours under the same conditions as in section 1, except that each siRNA was mixed with 1 µL of a Dharmacon transfection reagent (Dharmacon), and added to media. A negative control group was prepared in the same manner, except that scramble siRNA was added instead of the siRNAs. After culturing, PINT levels in the cells were measured in the same manner as in section 1. As a result, when siPINT-1, siPINT-2, siPINT-3, siPINT-4, and siPINT-5 were used, the PINT levels were decreased by 36, 0, 67, 50, and 0%, respectively, as compared to the control group. Among them, siPINT-3 and siPINT-4, which were the most effectively decreased the PINT levels, were used in the following experiment.

(3.2) DNA Damage by Inhibition of PINT Expression

HDF(neonatal) young cells being passaged 9 times and having a doubling time of 1 day and HDF(neonatal) senescent cells being passaged 49 times and having a doubling time of 14 days, which were prepared in section 1, were cultured for 72 hours under the same conditions as in section 1, except that each 25 nM of siPINT-3 and siPINT-4 was mixed with 1 µL of a Dharmacon transfection reagent (Dharmacon) and added to media. A negative control group was prepared in the same manner, except that scramble siRNA (hereinafter, also called 'siCTRL') was added instead of the siRNAs.

After culturing, proteins were isolated from siRNA-introduced cells, and then the isolated proteins were subjected to immunoblotting using anti-GAPDH and anti-phosphorylated-H2AX. H2AX becomes phosphorylated on serine 139 as a reaction on DNA Double-strand breaks (DSB), and is also called gamma-H2AX. Gamma-H2AX is an indicator of DNA damage.

Figure 3:
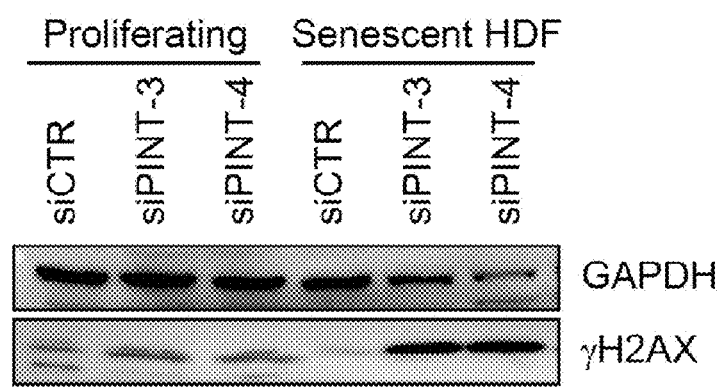
FIG. 3 shows results of measuring DNA damage in siRNA-introduced young and senescent cells.

FIG. 3 shows results of measuring DNA damage in siRNA-introduced young and senescent cells. As shown in FIG. 3, gamma-H2AX levels were specifically increased in siPINT-3 or siPINT-4-introduced senescent cells, indicating increased DNA damage. That is, siRNA specifically induced DNA damage in senescent cells.

Further, DNAs were isolated from the same cells, followed by DNA comet assay. This method is performed by detecting DNA strand break in cells, based on gel electrophoresis. During electrophoresis, damaged DNA shows a longer migration distance than non-damaged DNA to form a comet tail shape. After staining a slide with SYBR Green, a length of a tail of DNA fragment was measured under a fluorescence microscope to examine DNA damage.

FIG. 4 shows results of comet assay of measuring DNA damage in young cells and senescent cells by siRNA. In FIG. 4, the left (A) is a photograph showing the result of electrophoresis of DNA, in which proliferating HDF represents non-introduced HDF(neonatal) young cells which were passaged 9 times and had a doubling time of 1 day, that is, siCTRL-introduced cells, and senescent HDF siCTRL and senescent HDF siPINT represent those prepared by introducing siCTRL and siPINT-3 into HDF(neonatal) senescent cells which were passaged 49 times and had a doubling time of 14 days, respectively.

As shown in A of FIG. 4, senescent cells showed longer comet tails than young cells, indicating increased DNA damage. siPINT-3-introduced senescent cells showed remarkably increased DNA damage, compared to senescent cells without siPINT introduction. In FIG. 4, (B) shows the result of measuring tails (tail moment) on the photograph of DNA electrophoresis. As shown in B of FIG. 4, young cells, control senescent cells, siPINT-3-introduced senescent cells, and siPINT-4-introduced senescent cells showed tail moments of 0.52, 2.86, 3.68, and 5.58, respectively. The tail moments were greatly increased in siPINT-3- and siPINT-4-introduced senescent cells, indicating remarkably increased DNA damage.

(3.3) Selective Death of Senescent Cells by Inhibition of PINT Expression

HDF(neonatal) young cells being passaged 9 times and having a doubling time of 1 day and HDF(neonatal) senescent cells being passaged 49 times and having a doubling time of 14 days, which were prepared in section 1, were transfected with each of siPINT-1, siPINT-2, siPINT-3, siPINT-4, and siPINT-5 in the same manner as in section 3.2, and further cultured in wells of 6-well plates for 14 days under the same conditions as in section 1. A negative control group was prepared in the same manner, except that scramble siRNA (hereinafter, also called 'siCTR') was added instead of the siRNAs.

Figure 5:
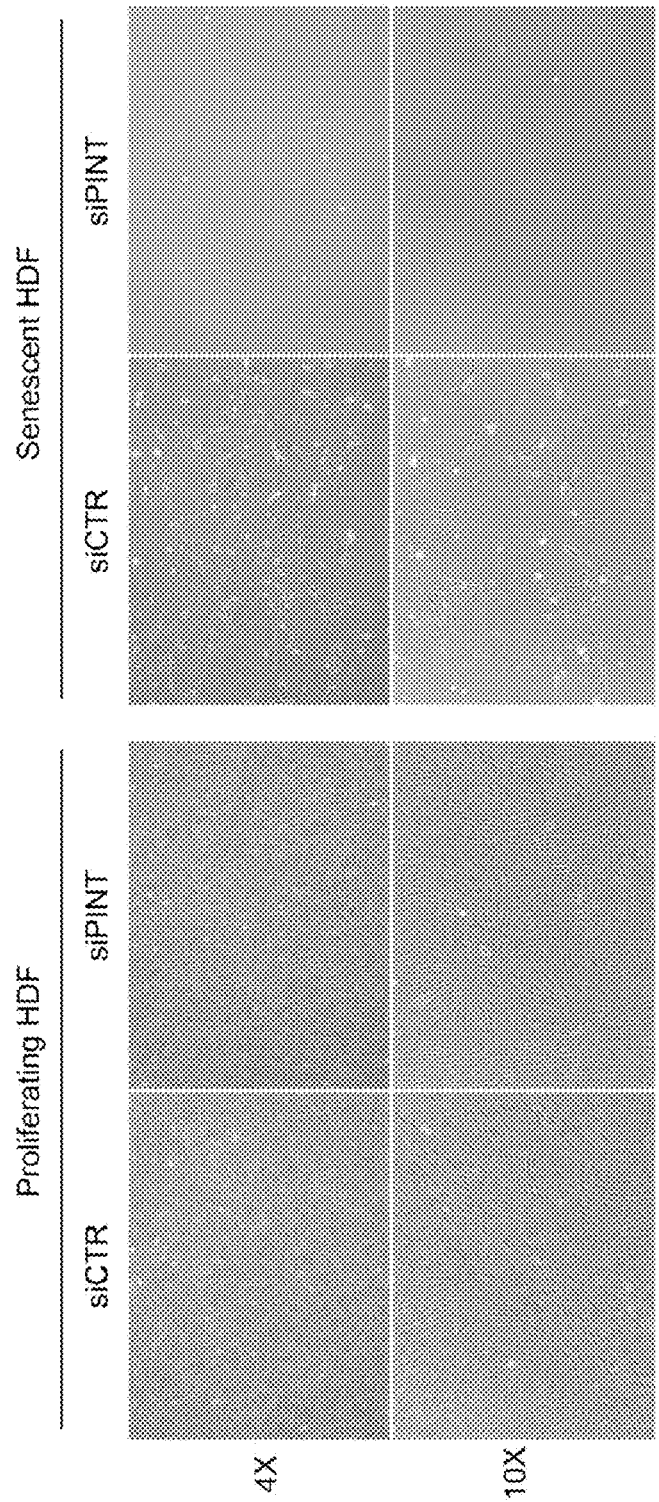
FIG. 5 shows photographs of siRNA-introduced young and senescent cells after culturing.

FIG. 5 shows photographs of siRNA-introduced young and senescent cells after culturing. In FIG. 5, siCTR represents control siRNA, and siPINT represents siPINT-3 among the five used siPINTs. As shown in FIG. 5, the number of senescent cells was remarkably decreased by inhibition of PINT lincRNA expression, compared to the negative control group, and also, living cells were unhealthy. However, there was little change in the number of young cells by inhibition of PINT lincRNA expression. This indicates that inhibiting PINT lincRNA expression specifically reduces the number of senescent cells. These results suggest that intracellular PINT lincRNA expression levels may be controlled by using PINT lincRNA expression inhibitors, thereby specifically inducing death of senescent cells, and ultimately, applied to the treatment of diseases associated with senescence and functional recovery of tissues and subjects having increased senescent cells.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A composition comprising one or more of an expression inhibitor inhibiting p53 induced non-coding transcript (PINT) gene expression or an activity inhibitor inhibiting PINT activity, wherein the expression inhibitor or activity inhibitor comprises an siRNA that comprises a pair of nucleotide sequences selected from the group consisting of SEQ ID NO: 12 and SEQ ID NO: 13; SEQ ID NO: 16 and SEQ ID NO: 17; and SEQ ID NO: 18 and SEQ ID NO: 19.

2. The composition of claim 1, further comprising a pharmaceutically acceptable carrier.

3. A method of killing senescent cells in a subject, the method comprising inhibiting p53-induced non-coding transcript (PINT) gene expression or inhibiting PINT activity in the senescent cells by administering to the cells the composition of claim 1.

4. The method of claim 3, wherein the PINT expression inhibitor and/or the PINT activity inhibitor is administered with a pharmaceutically acceptable carrier.

5. The method of claim 3, wherein the composition is topically administered to a senescent site.

6. The method of claim 5, wherein the senescent site is a site on the skin which has wrinkles, freckles, pigmentation spots, or a combination thereof.

* * * * *

SEQUENCE LISTING

```
<160> NUMBER OF SEQ ID NOS: 23

<210> SEQ ID NO 1
<211> LENGTH: 3273
<212> TYPE: DNA
<213> ORGANISM: Homo sapiens

<400> SEQUENCE: 1 ttggcccac  tgtgcaccac  acactccttt  cccagcccag  gggcacgcga  acaaaatgag    60
gctcaagctg  accaggccga  gccggaggaa  cgctggggct  tggcagcaga  agggatggga   120
ccagagagaa  gggtgtggag  gagaccccag  tgagggccaa  gacatttcag  gtaaagagag   180
gtcatatctc  cgtacctcac  ttcctgacac  aaacaagttt  tcactgttgt  cagcaacaaa   240
gccctaatat  agctgcggaa  gagaaaaact  gcattgcatt  ttgcctcctg  caagcatcat   300
caacagttac  tggaggaacg  taattccaga  aagcttgaaa  gccgtggtga  tggtaattat   360
gtatcaaatg  cctggttcta  tttctgttat  tattgttttg  tcatttctgt  tttcccagcg   420
atctgactga  actcgcagag  ggacaaatcc  agttttctt  tttgacttt   gtcaaactaa   480 atcaggcctg  atagaaaact  cattgctctc  cggggaaaca  aagtaggagc  cacgaaatgt   540
cattttaaca  gagcgtgggt  ttggtgactg  taggaaagga  tttgaggacg  ctccttctgt   600
tcggcttcct  atgtcatgag  cacaggctcc  acgcacgcac  agacaccacg  gctcccggat   660
gctgtggctc  cccgatcggg  gctcctgcag  cgccagaagc  ccctccggga  tgcttcgagg   720
ggctcccggt  gggtggaggt  acggacgccg  ctgcggccgc  cgccgccagt  cctgctgctg   780
ttgttgctgc  tgcagtcacg  tgggagcccc  tttaagtttc  catagagagg  cctctctggt   840
gtcacatgat  ggacatgata  taatgaaaca  acattgtgga  gaggaaagca  ttagggagc    900 ccacggctac  aaaaacaagt  gagtgagaag  aggtgggagg  aagagaaact  acgccacctc   960
ccctgcagcc  gagtgcacgc  agcagcctgg  cgtgacaagt  gggcgacgcc  gggggcagg   1020 gagccggggt  ccttggccct  ggccggggac  cccaccgccc  accgcgcgga  ggacaacttt  1080
tagccggcag  cccagaccag  cgcggcacct  gtctccggag  tctccaccgc  tcctcccgat  1140
tcatcccagg  gaaattctca  agaatacgct  ctacaaatct  acgtgcgcat  cattttcacc  1200
tcgcgtcgcg  cccgggagga  aggaacgagg  caaggagcta  aagcagcgtg  cgttcagccc  1260
```

```
tggggcattt tattaatgct tttacgagtt agaagagttg ggataatttg ccatctggag    1320
tttctctgcc ttgctgatct gagctcagac ctgccaattt accagagata attgataaca    1380
ccctgtaaca gctgagagga aaatggaaga acggagata cttttagtga agcagaataa     1440
accactgaac agtctgtttc atcttcataa aaacgctgct ttcagtgcac tggatttatt    1500
ttacaaccca ctaatggatt accctacagt ttgaaaaaca ttgcgttaga ccagtttgac    1560
tgttgtcaag aaccaaaaaa ggaaaaatga ggaagctgtg agtaccagtg aaggaacga     1620 gccaggaaga gggactggaa ccatctcaga agccatgccc ctcaggctgg aacttgccct    1680
gtctcctcgc agatgaggta ggaggctcag cacgggctgg tgggagcagc ccacagcagc    1740
agtgagggtc agtgggcctg tgagttaaga agaaggtggc acagagcgag ggtctctgga    1800
tcctgactgt ttgactttc catgattagg ataagtagcc agggcttggc tagttggaga    1860
gttactcgaa cctcaggtga cagttgtaag gcagcacata gtgaaaaaga gtcctagcct    1920
gggaaagtcc aaaaccttag gtctggtttc agttcactca cctatctctg tgacatagca    1980
aagtctgtta atttctctaa ttttctgatt agtagtatag ttgcaggaat gaaataaaaa    2040
tggtcctgat tactcagaga ttcatttact gattactctt tttgtgacct gaataaagag    2100
tacaacatct ctcaaaaggt aacaaatga tgtttcagga aattagagaa gttaagagac     2160
tttgctgtat ttactataca gatagttgac tgacagctga gcccggaccc aagattcatt    2220
tataaaatga aggagttgag aagtacatac tctgaggttt atcctaaata aactgaagtc    2280
taggcaagtg gctgagctag gtttgccatg aatcaatctg ctgagtatat ttcttggtaa    2340
ctagttcatc tttccttaat tcagtcaaca aatatgatat caagtttagt aagatgatga    2400
cagttgtcat gtaatactcc atctggaaga ttgtatgctt ctcagcttcc ctaactttc     2460 ttaatctacc ttaagcttcc tttctgaaag gtttctgtct ttcctaacag tctcttcttt    2520
ccgccagcta cctcttgtgt ttaagaatta aggaagatg agctaggaat caagaaatac     2580
gcagaactga ttcctgtcac tggcgccacc ctgccacttg cccagagctg tggtataaat    2640
ttttttaata ggctgaaata aaaatatgaa tagcattttg gtattaagca ttaaattgat    2700
aaaggctatg agatacacct gctctcaacc atgttaattt tttattattg gtattaataa    2760
attattactt actaacatat taacaagaat tgcattgaga acaaagcat ccacaggcca     2820 aatcttctga atttcaaatg tttatattaa tgcgttgtat tctagaaaag tagaattgtc    2880
ttaagtagct ttgtaatata aagtcatcta tcagcccatt acacctatta gaatgtttta    2940
acctttattt cccactttt tgtttctaga ctgagtgtac ttggtctggt atttgtggca    3000
taacttacgg aacacataag aatgatacag atactattta atgatgacct aatacaagct    3060
tagatagcta aggtgaaagc ttctatggcc ttaacatttt cctcttgaag aatgtatttt    3120
ctgtaataaa atacagtggc tacttgaaat ctataaactt atgtgaggtc tggataaatc    3180
tgagcaactt tcttctttgt gctccaggaa cctacgcact atatatataa ataaagctta    3240
agtaaacatc actgcaaaaa aaaaaaaaa aaa                                   3273

<210> SEQ ID NO 2
<211> LENGTH: 3144
<212> TYPE: DNA
<213> ORGANISM: Homo sapiens

<400> SEQUENCE: 2
ttggccccac tgtgcaccac acactccttt cccagcccag ggcacgcga acaaaatgag     60 gctcaagctg accaggccga gccggaggaa cgctggggct tggcagcaga agggatggga    120
```

```
ccagagagaa gggtgtggag gagacccccag tgagggccag gacatttcag gtaaagagag      180
gtcatatctc cgtacctcac ttcctgacac aaacaagttt tcactgttgt cagcaacaaa      240
gccctaatat agctgcggaa gagaaaaact gcattgcatt ttgcctcctg caagcatcat      300
caacagttac tggaggaacg taattccaga agcttgaaa  gccgtggtga tggtaattat      360
gtatcaaatg cctggttcta tttctgttat tattgttttg tcatttctgt tttcccagcg      420
atctgactga actcgcagag ggacaaatcc agttttcctt tttgactttt gtcaaactaa      480
atcaggcctg atagaaaact cattgctctc cggggaaaca agtaggagc  cacgaaatgt      540 cattttaaca gagcgtgggt ttggtgactg taggaaagga tttgaggacg ctccttctgt      600
tcggcttcct atgtcatgag cacaggctcc acgcacgcac agacaccacg gctcccggat      660
gctgtggctc cccgatcggg gctcctgcag cgccagaagc ccctccggga tgcttcgagg      720
ggctcccggt gggtggaggt acggacgccg ctgcggccgc cgccgccagt cctgctgctg      780
ttgttgctgc tgcagtcacg tgggagcccc tttaagtttc catagagagg cctctctggt      840
gtcacatgat ggacatgata taatgaaaca acattgtgga gaggaaagca ttaggggagc      900
ccacggctac aaaaacaagt gagtgagaag aggtgggagg aagagaaact acgccacctc      960
ccctgcagcc gagtgcacgc agcagcctgg cgtgacaagt gggcgacgcc gggggcagg     1020 gagccggggt ccttggccct ggccggggac cccaccgccc accgcgcgga ggacaacttt     1080
tagccggcag cccagaccag cgcggcacct gtctccggag tctccaccgc tcctcccgat     1140
tcatcccagg gaaattctca agaatacgct ctacaaatct acgtgcgcat cattttcacc     1200
tcgcgtcgcg cccgggagga aggaacgagg caaggagcta aagcagcgtg cgttcagccc     1260
tggggcattt tattaatgct tttacgagtt agaagagttg ggataatttg ccatctggag     1320
tttctctgcc ttgctgatct gagctcagac ctgccaattt accagagata attgataaca     1380
ccctgtaaca gctgagagga aaatggaaga aacggagata cttttagtga agcagaataa     1440
accactgaac aggaaaaatg aggaagctgt gagtaccagt ggaaggaacg agccaggaag     1500
agggactgga accatctcag aagccatgcc cctcaggctg gaacttgccc tgtctcctcg     1560
cagatgaggt aggaggctca gcacgggctg gtgggagcag cccacagcag cagtgagggt     1620
cagtgggcct gtgagttaag aagaaggtgg cacagagcga gggtctctgg atcctgactg     1680
tttgactttt ccatgattag gataagtagc cagggcttgg ctagttggag agttactcga     1740
acctcaggtg acagttgtaa ggcagcacat agtgaaaaag agtcctagcc tgggaaagtc     1800 caaaaccttag ggtctggttt cagttcactc acctatctct gtgacatagc aaagtctgtt     1860
aatttctcta attttctgat tagtagtata gttgcaggaa tgaaataaaa atggtcctga     1920
ttactcagag attcatttac tgattactct ttttgtgacc tgaataaaga gtacaacatc     1980
tctcaaaagg taacaatatg atgtttcagg aaattagaga agttaagaga ctttgctgta     2040
tttactatac agatagttga ctgacagctg agcccggacc caagattcat ttataaaatg     2100
aaggagttga gaagtacata ctctgaggtt tatcctaaat aaaactgaagt ctaggcaagt     2160 ggctgagcta ggttttgccat gaatcaatct gctgagtata tttcttggta actagttcat     2220
ctttccttaa ttcagtcaac aaatatgata tcaagtttag taagatgatg acagttgtca     2280
tgtaatactc catctggaag attgtatgct tctcagcttc cctaactttt cttaatctac     2340
cttaagcttc ctttctgaaa ggtttctgtc tttcctaaca gtctcttctt tccgccagct     2400
acctcttgtg tttaagaatt aaaggaagat gagctaggaa tcaagaaata cgcagaactg     2460
```

-continued

| | |
|---|---|
| attcctgtca ctggcgccac cctgccactt gcccagagct gtggtataaa ttttttttaat | 2520 |
| aggctgaaat aaaaatatga atagcatttt ggtattaagc attaaattga taaaggctat | 2580 |
| gagatacacc tgctctcaac catgttaatt ttttattatt ggtattaata aattattact | 2640 |
| tactaacata ttaacaagaa ttgcattgag aaacaaagca tccacaggcc aaatcttctg | 2700 |
| aatttcaaat gtttatatta atgcgttgta ttctagaaaa gtagaattgt cttaagtagc | 2760 |
| tttgtaatat aaagtcatct atcagcccat tacacctatt agaatgtttt aacctttatt | 2820 |
| tcccactttt ttgtttctag actgagtgta cttggtctgg tatttgtggc ataacttacg | 2880 |
| gaacacataa gaatgataca gatactattt aatgatgacc taatacaagc ttagatagct | 2940 |
| aaggtgaaag cttctatggc cttaacattt tcctcttgaa gaatgtattt tctgtaataa | 3000 |
| aatacagtgg ctacttgaaa tctataaact tatgtgaggt ctggataaat ctgagcaact | 3060 |
| ttcttctttg tgctccagga acctacgcac tatatatata aataaagctt aagtaaacat | 3120 |
| cactgcaaaa aaaaaaaaaa aaaa | 3144 |

<210> SEQ ID NO 3
<211> LENGTH: 1280
<212> TYPE: DNA
<213> ORGANISM: Homo sapiens

<400> SEQUENCE: 3

| | |
|---|---|
| actggaatca gcaactccct ggaactcggg cctctggccc cgtccctctt ttctccggca | 60 |
| gggacgcagg atgccttggt gcactctaga cggggacc ggagggtgca gcgcgcctgg | 120 |
| gtggggcgaa gggcgccggt ctcctcacgc cctctgactt taggatacca gacagtgtct | 180 |
| cttcaacccc accccaggcg caggtttcca gaaggcgggg tgggtggggc cccgatttc | 240 |
| cagaaggcga gttacctagc aggtgtgtgg ggtgggcatt gctattcgga gaaaaatcaa | 300 |
| gacgttccct tcagtcctcc ctcggtgtta acgtctgctc cagctcgcag cccgctgctg | 360 |
| ggaggaaaat ggaagaaacg gagatacttt tagtgaagca gaataaacca ctgaacagga | 420 |
| aaaatgagga agctgtgagt accagtggaa ggaacgagcc aggaagaggg actggaacca | 480 |
| tctcagaagc catgccctc aggctggaac ttgccctgtc tcctcgcaga tgagctacct | 540 |
| cttgtgttta agaattaaag gaagatgagc taggaatcaa gaaatacgca gaactgattc | 600 |
| ctgtcactgg cgccaccctg ccacttgccc agagctgtgg tataaatttt tttaataggc | 660 |
| tgaaataaaa atatgaatag cattttggta ttaagcatta aattgataaa ggctatgaga | 720 |
| tacacctgct ctcaaccatg ttaatttttt attattggta ttaataaatt attacttact | 780 |
| aacatattaa caagaattgc attgagaaac aaagcatcca caggccaaat cttctgaatt | 840 |
| tcaaatgttt atattaatgc gttgtattct agaaaagtag aattgtctta agtagctttg | 900 |
| taatataaag tcatctatca gcccattaca cctattagaa tgttttaacc tttatttccc | 960 |
| acttttttgt ttctagactg agtgtacttg gtctggtatt tgtggcataa cttacggaac | 1020 |
| acataagaat gatacagata ctatttaatg atgacctaat acaagcttag atagctaagg | 1080 |
| tgaaagcttc tatggcctta acattttcct cttgaagaat gtattttctg taataaaata | 1140 |
| cagtggctac ttgaaatcta taaacttatg tgaggtctgg ataaatctga gcaacttct | 1200 |
| tctttgtgct ccaggaacct acgcactata tatataaata agcttaagt aaacatcact | 1260 |
| gcaaaaaaaa aaaaaaaaa | 1280 |

<210> SEQ ID NO 4
<211> LENGTH: 2228

<212> TYPE: DNA
<213> ORGANISM: Homo sapiens

<400> SEQUENCE: 4

```
aaacagcgat tcttctgcag tgaatcactt ccagaaatga atagccacag ttttttggaa      60
tgaacgttgt gaaatccctc ctttataatg gcaggttttc agttggtggt tttatcagaa     120
tttctcaaga tcaaaacgaa accttctctt taaaaaggaa agaaagtact atcgatacag     180
aaagcaaaag tatttccagt ctcctactga actgtcacgg cagacctctc tgtatctata     240
tttagagctg tatgtccata tatttgcctg aatgtgtgag ttcttggaag tatggattca     300
ttgccaggag ctggtgattt cctaagcaga ggtcgctaac tacaagaaat gttacactcg     360
gacaagtcct gcgcttgggg atcctctgta cgcccgttca ctggtgcagg tcttctgaac     420
aaatgcctcc tgaggatttc tgtgcctgga aaatatctgt taacagactg cttttacacc     480
tacctatttg gtgctacttc tactcctcat gaccaaagct ggctttcatg gtttactcat     540
gtacttactg atgaaaccct gagacttggg gccagtgact gttcagaggt ccatgtgaag     600
atgcgctgaa tggtataaag gacagagcag taaagagtgc tggctgaatg cctgggctgg     660
caatcaggca tgttggagtt tgagtcccag tctgccactc cagctctgtg accaagagga     720
agtgaagtca tgtaccctt ctaagtctct agcccctctt ctgaaagacg aagatgccac     780
caccaaccat gttagtggtt gtgaatgcca agaaagtcca tgtgaagcac atagcatagt     840
gtctgccatg cgttaagtgt tccaaaaatg gaagctatga ctatttcaca gagtacactt     900
cccatcactt ttcagttcat tttggccttc tccctcaaaa gcactccagt gttctgatcc     960
agctgataaa acaccaaaca ttcacatagt gctttaaaag tgacccactg tttttacaga    1020
ctgcattaca tatgacccta caaccactg caatatagaa attcgcatct ccattctcca    1080
gatcaggata ccgaagctca gaaaaattaa atgatttgcc caggatcaca tagttagtaa    1140
gcagcccagc cagatcctgt gttaacttgt tcatccgctt cctataagaa acatccatt    1200
caaggcacat ggggcaacaa agaaggactt agagctgtgt ggcccctcgt cagggcagta    1260
ccagttgcac ccatagtccg gcctgaatac tcagcttagg actattgtgt ccaatgtccc    1320
aaacattttg aagctacatc ttaaagaagt gtcctgctca gatgcagttc tccttgtgaa    1380
atccgcaggc cccaaggaaa gtgactttaa tccagtttgc tcatgcaaga acagactggc    1440
atttcacatc caggaaaaca atggatttgt actgttcagc ttttgccatg caaggagttc    1500
ctggtgtggt ttattaattt acatctcagg ctccagcttc actatcaatc agatttggaa    1560
gaaaaaagtt acaagaaag gcagcttgct gagaaacagc ggaagcatga cggtacagac    1620
tgggttttga aatggagaca cattctcatg gcttgtgggc tgagagacac tgagaaagga    1680
ttttgttctt gaaagatgat tgtttttaatg ctggagatgg agagtttga caattttaag    1740
tgcatgttct gtgtgtaaga aagagtcatt acgttttttt tttctttcag atgttgccat    1800
gccttaaaat tgctgatgat taaaatagaa catcctgagt tacagaaatt cagcccctagt    1860
gtatcctggc ctaaaaatac agaacaatca agttgattgt tggaaatgag aggctaggca    1920
gggttggaaa catgctaatg tttactgagt gaaatctttc cttctcagta gagttgccct    1980
tgcagctgaa agtcactgaa agactcaaca aaataagcag atcccacttg tctcactctg    2040
ttctcctatg catgccctgg aaagagaatg aatgagccct ttttaattta tcaactggtt    2100
ttcttccatc tctttactag tgagccatgg gggtttttg ccgttaactg ggtagccagt    2160
ctcttcatgg agacttattt tcaggaaact agcctcttgc tttatgtgaa aacaaggacc    2220
```

| | |
|---|---:|
| caactcaa | 2228 |

<210> SEQ ID NO 5
<211> LENGTH: 3268
<212> TYPE: DNA
<213> ORGANISM: Homo sapiens

<400> SEQUENCE: 5

| | |
|---|---:|
| ttggccccac tgtgcaccac acactccttt cccagcccag gggcacgcga acaaaatgag | 60 |
| gctcaagctg accaggccga gccggaggaa cgctggggct tggcagcaga agggatggga | 120 |
| ccagagagaa gggtgtggag gagaccccag tgagggccag acatttcag gtaaagagag | 180 |
| gtcatatctc cgtacctcac ttcctgacac aaacaagttt tcactgttgt cagcaacaaa | 240 |
| gccctaatat agctgcggaa gagaaaaact gcattgcatt tgcctcctg caagcatcat | 300 |
| caacagttac tggaggaacg taattccaga aagcttgaaa gccgtggtga tggtaattat | 360 |
| gtatcaaatg cctggttcta tttctgttat tattgttttg tcatttctgt tttcccagcg | 420 |
| atctgactga actcgcagag ggacaaatcc agttttctt tttgacttt gtcaaactaa | 480 |
| atcaggcctg atagaaaact cattgctctc cggggaaaca agtaggagc acgaaatgt | 540 |
| cattttaaca gagcgtgggt ttggtgactg taggaaagga tttgaggacg ctccttctgt | 600 |
| tcggcttcct atgtcatgag cacaggctcc acgcacgcac agacaccacg gctcccggat | 660 |
| gctgtggctc cccgatcggg gctcctgcag cgccagaagc cctccggga tgcttcgagg | 720 |
| ggctcccggt gggtggaggt acggacgccg ctgcggccgc cgccgccagt cctgctgctg | 780 |
| tgttgctgc tgcagtcacg tgggagcccc tttaagtttc catagagagg cctctctggt | 840 |
| gtcacatgat ggacatgata taatgaaaca acattgtgga gaggaaagca ttaggggagc | 900 |
| ccacggctac aaaaacaagt gagtgagaag aggtgggagg aagagaaact acgccacctc | 960 |
| ccctgcagcc gagtgcacgc agcagcctgg cgtgacaagt gggcgacgcc ggggggcagg | 1020 |
| gagccggggt ccttggccct ggccggggac cccaccgccc accgcgcgga ggacaacttt | 1080 |
| tagccggcag cccagaccag cgcggcacct gtctccggag tctccaccgc tcctcccgat | 1140 |
| tcatcccagg gaaattctca agaatacgct ctacaaatct acgtgcgcat cattttcacc | 1200 |
| tcgcgtcgcg cccgggagga aggaacgagg caaggagcta agcagcgtg cgttcagccc | 1260 |
| tggggcattt tattaatgct tttacgagtt agaagagttg ggataatttg ccatctggag | 1320 |
| tttctctgcc ttgctgatct gagctcagac ctgccaattt accagagata attgataaca | 1380 |
| ccctgtaaca gctgaagaca gagtcttacc ctgtcaccca ggctggagta caatggtgcg | 1440 |
| atctcggctc actgcaacct ctgcctcctg ggttcaagtg attcttctgc ctcagcctcc | 1500 |
| tgagtagctg ggactacagg aggaaaatgg aagaaacgga gatacttta gtgaagcaga | 1560 |
| ataaaccact gaacaggaaa aatgaggaag ctgtgagtac cagtggaagg aacgagccag | 1620 |
| gaagagggac tggaaccatc tcagaagcca tgccctcag gctggaactt gccctgtctc | 1680 |
| ctcgcagatg aggtaggagg ctcagcacgg gctggtggga gcagcccaca gcagcagtga | 1740 |
| gggtcagtgg gcctgtgagt taagaagaag gtggcacaga gcgagggtct ctggatcctg | 1800 |
| actgtttgac ttttccatga ttaggataag tagccagggc ttggctagtt ggagagttac | 1860 |
| tcgaacctca ggtgacagtt gtaaggcagc acatagtgaa aaagagtcct agcctgggaa | 1920 |
| agtccaaaac cttaggtctg gtttcagttc actcacctat ctctgtgaca tagcaaagtc | 1980 |
| tgttaatttc tctaatttc tgattagtag tatagttgca ggaatgaaat aaaaatggtc | 2040 |
| ctgattactc agagattcat ttactgatta ctcttttgt gacctgaata aagagtacaa | 2100 |

```
catctctcaa aaggtaacaa tatgatgttt caggaaatta gagaagttaa gagactttgc    2160
tgtatttact atacagatag ttgactgaca gctgagcccg gacccaagat tcatttataa    2220
aatgaaggag ttgagaagta catactctga ggtttatcct aaataaactg aagtctaggc    2280
aagtggctga gctaggtttg ccatgaatca atctgctgag tatatttctt ggtaactagt    2340
tcatctttcc ttaattcagt caacaaatat gatatcaagt ttagtaagat gatgacagtt    2400
gtcatgtaat actccatctg gaagattgta tgcttctcag cttccctaac ttttcttaat    2460
ctaccttaag cttcctttct gaaaggtttc tgtctttcct aacagtctct tctttccgcc    2520
agctacctct tgtgtttaag aattaaagga agatgagcta ggaatcaaga aatacgcaga    2580
actgattcct gtcactggcg ccaccctgcc acttgcccag agctgtggta taaattttt    2640 taataggctg aaataaaaat atgaatagca ttttggtatt aagcattaaa ttgataaagg    2700
ctatgagata cacctgctct caaccatgtt aattttttat tattggtatt aataaattat    2760
tacttactaa catattaaca agaattgcat tgagaaacaa agcatccaca ggccaaatct    2820
tctgaatttc aaatgtttat attaatgcgt tgtattctag aaaagtagaa ttgtcttaag    2880
tagctttgta atataaagtc atctatcagc ccattacacc tattagaatg ttttaacctt    2940
tatttcccac ttttttgttt ctagactgag tgtacttggt ctggtatttg tggcataact    3000 tacgaacac ataagaatga tacagatact atttaatgat gacctaatac aagcttagat    3060
agctaaggtg aaagcttcta tggccttaac attttcctct tgaagaatgt attttctgta    3120
ataaaataca gtggctactt gaaatctata aacttatgtg aggtctggat aaatctgagc    3180
aactttcttc tttgtgctcc aggaacctac gcactatata tataaataaa gcttaagtaa    3240
acatcactgc aaaaaaaaaa aaaaaaa                                        3268

<210> SEQ ID NO 6
<211> LENGTH: 3246
<212> TYPE: DNA
<213> ORGANISM: Homo sapiens

<400> SEQUENCE: 6
ttggccccac tgtgcaccac acactccttt cccagcccag gggcacgcga acaaaatgag      60
gctcaagctg accaggccga gccggaggaa cgctggggct tggcagcaga agggatggga    120
ccagagagaa gggtgtggag gagacccag tgagggccag acatttcag gtaaagagag    180 gtcatatctc cgtacctcac ttcctgacac aaacaagttt tcactgttgt cagcaacaaa    240
gccctaatat agctgcggaa gagaaaaact gcattgcatt ttgcctcctg caagcatcat    300
caacagttac tggaggaacg taattccaga aagcttgaaa gccgtggtga tggtaattat    360
gtatcaaatg cctggttcta tttctgttat tattgttttg tcatttctgt tttcccagcg    420
atctgactga actcgcagag ggacaaatcc agttttcttt tttgactttt gtcaaactaa    480
atcaggcctg atagaaaact cattgctctc cggggaaaca aagtaggagc cacgaaatgt    540 catttaaca gagcgtgggt ttggtgactg taggaaagga tttgaggacg ctccttctgt    600
tcggcttcct atgtcatgag cacaggctcc acgcacgcac agacaccacg gctcccggat    660
gctgtggctc cccgatcggg gctcctgcag cgccagaagc cctccggga tgcttcgagg    720 ggctcccggt gggtggaggt acggacgccg ctgcggccgc cgccgccagt cctgctgctg    780
ttgttgctgc tgcagtcacg tgggagcccc tttaagtttc catagagagg cctctctggt    840
gtcacatgat ggacatgata taatgaaaca acattgtgga gaggaaagca ttaggggagc    900
```

-continued

```
ccacggctac aaaaacaagt gagtgagaag aggtgggagg aagagaaact acgccacctc    960
ccctgcagcc gagtgcacgc agcagcctgg cgtgacaagt gggcgacgcc gggggcagg    1020
gagccgggt ccttggccct ggccggggac cccaccgccc accgcgcgga ggacaacttt    1080
tagccggcag cccagaccag cgcggcacct gtctccggag tctccaccgc tcctcccgat    1140
tcatcccagg gaaattctca agaatacgct ctacaaatct acgtgcgcat cattttcacc    1200
tcgcgtcgcg cccgggagga aggaacgagg caaggagcta aagcagcgtg cgttcagccc    1260
tggggcattt tattaatgct tttacgagtt agaagagttg ggataatttg ccatctggag    1320
tttctctgcc ttgctgatct gagctcgac ctgccaattt accagagata attgataaca    1380
ccctgtaaca gctgagagga aaatggaaga aacggagata cttttagtga agcagaataa    1440
accactgaac agatggagtc tcactctgtt gcccagactg gaatgcagtg gtgtgatctc    1500
aactgactgc aacctccgta tcctgggttc aagcaactct cctgctgcag ccacgaaaaa    1560
tgaggaagct gtgagtacca gtggaaggaa cgagccagga agagggactg gaaccatctc    1620
agaagccatg cccctcaggc tggaacttgc cctgtctcct cgcagatgag gtaggaggct    1680
cagcacgggc tggtgggagc agcccacagc agcagtgagg gtcagtgggc ctgtgagtta    1740
agaagaaggt ggcacagagc gagggtctct ggatcctgac tgtttgactt ttccatgatt    1800
aggataagta gccagggctt ggctagttgg agagttactc gaacctcagg tgacagttgt    1860
aaggcagcac atagtgaaaa agagtcctag cctgggaaag tccaaaacct taggtctggt    1920
ttcagttcac tcacctatct ctgtgacata gcaaagtctg ttaatttctc taattttctg    1980
attagtagta tagttgcagg aatgaaataa aaatggtcct gattactcag agattcattt    2040
actgattact cttttgtga cctgaataaa gagtacaaca tctctcaaaa ggtaacaata    2100
tgatgtttca ggaaattaga gaagttaaga gactttgctg tatttactat acagatagtt    2160
gactgacagc tgagcccgga cccaagattc atttataaaa tgaaggagtt gagaagtaca    2220
tactctgagg tttatcctaa ataaactgaa gtctaggcaa gtggctgagc taggtttgcc    2280
atgaatcaat ctgctgagta tatttcttgg taactagttc atctttcctt aattcagtca    2340
acaaatatga tatcaagttt agtaagatga tgacagttgt catgtaatac tccatctgga    2400
agattgtatg cttctcagct tccctaactt ttcttaatct accttaagct tcctttctga    2460
aaggtttctg tctttcctaa cagtctcttc tttccgccag ctacctcttg tgtttaagaa    2520
ttaaaggaag atgagctagg aatcaagaaa tacgcagaac tgattcctgt cactggcgcc    2580
accctgccac ttgcccagag ctgtggtata aattttttta ataggctgaa ataaaaatat    2640
gaatagcatt ttggtattaa gcattaaatt gataaaggct atgagataca cctgctctca    2700
accatgttaa tttttttatta ttggtattaa taaattatta cttactaaca tattaacaag    2760
aattgcattg agaaacaaag catccacagg ccaaatcttc tgaatttcaa atgtttatat    2820
taatgcgttg tattctagaa aagtagaatt gtcttaagta gctttgtaat ataaagtcat    2880
ctatcagccc attacaccta ttagaatgtt ttaacctta tttcccactt ttttgtttct    2940
agactgagtg tacttggtct ggtatttgtg gcataactta cggaacacat aagaatgata    3000
cagatactat ttaatgatga cctaatacaa gcttagatag ctaaggtgaa agcttctatg    3060
gccttaacat tttcctcttg aagaatgtat tttctgtaat aaaatacagt ggctacttga    3120
aatctataaa cttatgtgag gtctggataa atctgagcaa ctttcttctt tgtgctccag    3180
gaacctacgc actatatata taaataaagc ttaagtaaac atcactgcaa aaaaaaaaa    3240
aaaaaa                                                              3246
```

<210> SEQ ID NO 7
<211> LENGTH: 2314
<212> TYPE: DNA
<213> ORGANISM: Homo sapiens

<400> SEQUENCE: 7

| | | | | | | |
|---|---|---|---|---|---|---|
| ttggccccac | tgtgcaccac | acactccttt | cccagcccag | ggcacgcga | acaaaatgag | 60 |
| gctcaagctg | accaggccga | gccggaggaa | cgctggggct | tggcagcaga | agggatggga | 120 |
| ccagagagaa | gggtgtggag | gagaccccag | tgagggccag | gacatttcag | gtaaagagag | 180 |
| gtcatatctc | cgtacctcac | ttcctgacac | aaacaagttt | tcactgttgt | cagcaacaaa | 240 |
| gccctaatat | agctgcggaa | gagaaaaact | gcattgcatt | ttgcctcctg | caagcatcat | 300 |
| caacagttac | tggaggaacg | taattccaga | aagcttgaaa | gccgtggtga | tggtaattat | 360 |
| gtatcaaatg | cctggttcta | tttctgttat | tattgttttg | tcatttctgt | tttcccagcg | 420 |
| atctgactga | actcgcagag | ggacaaatcc | agttttctt | tttgactttt | gtcaaactaa | 480 |
| atcaggcctg | atagaaaact | cattgctctc | cggggaaaca | aagtaggagc | cacgaaatgt | 540 |
| cattttaaca | gagcgtgggt | ttggtgactg | taggaaagga | tttgaggacg | ctccttctgt | 600 |
| tcggcttcct | atgtcatgag | cacaggctcc | acgcacgcac | agacaccacg | gctcccggat | 660 |
| gctgtggctc | cccgatcggg | gctcctgcag | cgccagaagc | ccctccggga | tgcttcgagg | 720 |
| ggctcccggt | gggtggaggt | acggacgccg | ctgcggccgc | cgccgccagt | cctgctgctg | 780 |
| ttgttgctgc | tgcagtcacg | tgggagcccc | tttaagtttc | catagagagg | cctctctggt | 840 |
| gtcacatgat | ggacatgata | taatgaaaca | acattgtgga | gaggaaagca | ttaggggagc | 900 |
| ccacggctac | aaaacaagt | gagtgagaag | aggtgggagg | aagagaaact | acgccacctc | 960 |
| ccctgcagcc | gagtgcacgc | agcagcctgg | cgtgacaagt | gggcgacgcc | gggggcagg | 1020 |
| gagccgggt | ccttggccct | ggccggggac | cccaccgccc | accgcgcgga | ggacaacttt | 1080 |
| tagccggcag | cccagaccag | cgcggcacct | gtctccggag | tctccaccgc | tcctcccgat | 1140 |
| tcatcccagg | gaaattctca | agaatacgct | ctacaaatct | acgtgcgcat | cattttcacc | 1200 |
| tcgcgtcgcg | cccggggagga | aggaacgagg | caaggagcta | aagcagcgtg | cgttcagccc | 1260 |
| tggggcattt | tattaatgct | tttacgagtt | agaagagttg | ggataatttg | ccatctggag | 1320 |
| tttctctgcc | ttgctgatct | gagctcagac | ctgccaattt | accagagata | attgataaca | 1380 |
| ccctgtaaca | gctgagagga | aaatggaaga | aacggagata | cttttagtga | agcagaataa | 1440 |
| accactgaac | aggaaaaatg | aggaagctgt | gagtaccagt | ggaaggaacg | agccaggaag | 1500 |
| agggactgga | accatctcag | aagccatgcc | cctcaggctg | gaacttgccc | tgtctcctcg | 1560 |
| cagatgagct | acctcttgtg | tttaagaatt | aaaggaagat | gagctaggaa | tcaagaaata | 1620 |
| cgcagaactg | attcctgtca | ctggcgccac | cctgccactt | gcccagagct | gtggtataaa | 1680 |
| ttttttttaat | aggctgaaat | aaaaatatga | atagcatttt | ggtattaagc | attaaattga | 1740 |
| taaaggctat | gagatacacc | tgctctcaac | catgttaatt | tttattatt | ggtattaata | 1800 |
| aattattact | tactaacata | ttaacaagaa | ttgcattgag | aaacaaagca | tccacaggcc | 1860 |
| aaatcttctg | aatttcaaat | gtttatatta | atgcgttgta | ttctagaaaa | gtagaattgt | 1920 |
| cttaagtagc | tttgtaatat | aaagtcatct | atcagcccat | tacacctatt | agaatgtttt | 1980 |
| aacctttatt | tcccactttt | ttgtttctag | actgagtgta | cttggtctgg | tatttgtggc | 2040 |
| ataacttacg | gaacacataa | gaatgataca | gatactattt | aatgatgacc | taatacaagc | 2100 |

-continued

| | |
|---|---|
| ttagatagct aaggtgaaag cttctatggc cttaacattt tcctcttgaa gaatgtattt | 2160 |
| tctgtaataa aatacagtgg ctacttgaaa tctataaact tatgtgaggt ctggataaat | 2220 |
| ctgagcaact ttcttctttg tgctccagga acctacgcac tatatatata aataaagctt | 2280 |
| aagtaaacat cactgcaaaa aaaaaaaaaa aaaa | 2314 |

<210> SEQ ID NO 8
<211> LENGTH: 2270
<212> TYPE: DNA
<213> ORGANISM: Homo sapiens

<400> SEQUENCE: 8

| | |
|---|---|
| ttggccccac tgtgcaccac acactccttt cccagcccag ggcacgcga acaaaatgag | 60 |
| gctcaagctg accaggccga gccggaggaa cgctggggct tggcagcaga agggatggga | 120 |
| ccagagagaa gggtgtggag gagaccccag tgagggccag gacatttcag gtaaagagag | 180 |
| gtcatatctc cgtacctcac ttcctgcaca aaacaagttt tcactgttgt cagcaacaaa | 240 |
| gccctaatat agctgcggaa gagaaaaact gcattgcatt ttgcctcctg caagcatcat | 300 |
| caacagttac tggaggaacg taattccaga aagcttgaaa gccgtggtga tggtaattat | 360 |
| gtatcaaatg cctggttcta tttctgttat tattgttttg tcatttctgt tttcccagcg | 420 |
| atctgactga actcgcagag ggacaaatcc agtttttctt tttgacttttt gtcaaactaa | 480 |
| atcaggccta atagaaaact cattgctctc cggggaaaca aagtaggagc cacgaaatgt | 540 |
| cattttaaca gagcgtgggt ttggtgactg taggaaagga tttgaggacg ctccttctgt | 600 |
| tcggcttcct atgtcatgag cacaggctcc acgcacgcac agacaccacg gctcccggat | 660 |
| gctgtggctc cccgatcggg gctcctgcag cgccagaagc ccctccggga tgcttcgagg | 720 |
| ggctcccggt gggtggaggt acggacgccg ctgcggccgc cgccgccagt cctgctgctg | 780 |
| ttgttgctgc tgcagtcacg tgggagcccc tttaagtttc catagagagg cctctctggt | 840 |
| gtcacatgat ggacatgata taatgaaaca acattgtgga gaggaaagca ttaggggagc | 900 |
| ccacggctac aaaaacaagt gagtgagaag aggtgggagg aagagaaact acgccacctc | 960 |
| ccctgcagcc gagtgcacgc agcagcctgg cgtgacaagt gggcgacgcc ggggggcagg | 1020 |
| gagccggggt ccttggccct ggccggggac cccaccgccc accgcgcgga ggacaacttt | 1080 |
| tagccggcag cccagaccag cgcggcacct gtctccggag tctccaccgc tcctcccgat | 1140 |
| tcatcccagg gaaattctca agaatacgct ctacaaatct acgtgcgcat cattttcacc | 1200 |
| tcgcgtcgcg cccgggagga aggaacgagg caaggagcta aagcagcgtg cgttcagccc | 1260 |
| tggggcattt tattaatgct tttacgagtt agaagagttg ggataatttg ccatctggag | 1320 |
| tttctctgcc ttgctgatct gagctcagac ctgccaattt accagagata attgataaca | 1380 |
| ccctgtaaca gctgagagga aaatggaaga aacggagata cttttagtga agcagaataa | 1440 |
| accactgaac aggaagaggg actgaaacca tctcagaagc catgcccctc aggctggaac | 1500 |
| ttgccctgtc tcctcgcaga tgagctacct cttgtgttta agaattaaag gaagatgagc | 1560 |
| taggaatcaa gaaatacgca gaactgattc ctgtcactgg cgccaccctg ccacttgccc | 1620 |
| agagctgtgg tataaatttt tttaataggc tgaaataaaa atatgaatag cattttggta | 1680 |
| ttaagcatta aattgataaa ggctatgaga tacacctgct ctcaaccatg ttaattttt | 1740 |
| attattggta ttaataaatt attacttact aacatattaa caagaattgc attgagaaac | 1800 |
| aaagcatcca caggccaaat cttctgaatt tcaaatgttt atattaatgc gttgtattct | 1860 |
| agaaaagtag aattgtctta agtagctttg taatataaag tcatctatca gcccattaca | 1920 |

```
cctattagaa tgttttaacc tttatttccc acttttttgt ttctagactg agtgtacttg    1980
gtctggtatt tgtggcataa cttacggaac acataagaat gatacagata ctatttaatg    2040
atgacctaat acaagcttag atagctaagg tgaaagcttc tatggcctta acattttcct    2100
cttgaagaat gtattttctg taataaaata cagtggctac ttgaaatcta taaacttatg    2160
tgaggtctgg ataaatctga gcaactttct tctttgtgct ccaggaacct acgcactata    2220
tatataaata aagcttaagt aaacatcact gcaaaaaaaa aaaaaaaaa                2270
```

<210> SEQ ID NO 9
<211> LENGTH: 1536
<212> TYPE: DNA
<213> ORGANISM: Homo sapiens

<400> SEQUENCE: 9

```
ttggccccac tgtgcaccac acactccttt cccagcccag ggcacgcga acaaaatgag      60 gctcaagctg accaggccga gccggaggaa cgctggggct tggcagcaga agggatggga    120
ccagagagaa gggtgtggag gagaccccag tgagggccag gacatttcag gtaaagagag    180
gtcatatctc cgtacctcac ttcctgacac aaacaagttt tcactgttgt cagcaacaaa    240
gccctaatat agctgcggaa gagaaaaact gcattgcatt ttgcctcctg caagcatcat    300
caacagttac tggaggaacg taattccaga aagcttgaaa gccgtggtga tggtaattat    360
gtatcaaatg cctggttcta tttctgttat tattgttttg tcatttctgt tttcccagcg    420
atctgactga actcgcagag ggacaaatcc agttttcctt tttgacttt gtcaaactaa     480 atcaggcctg atagaaaact cattgctctc cggggaaaca agtaggagc cacgaaatgt     540 cattttaaca gagcgtgggt ttggtgactg taggaaagga tttgaggacg ctccttctgt    600
tcggcttcct atgtcatgag cacaggctcc acgcacgcac agacaccacg gctcccggat    660
gctgtggctc cccgatcggg gctcctgcag cgccagaagc ccctccggga tgcttcgagg    720
ggctcccggt gggtggaggt acggacgccg ctgcggccgc cgccgccagt cctgctgctg    780
ttgttgctgc tgcagtcacg tgggagcccc tttaagtttc catagagagg cctctctggt    840
gtcacatgat ggacatgata taatgaaaca acattgtgga gaggaaagca ttaggggagc    900
ccacggctac aaaaacaagt gagtgagaag aggtgggagg aagagaaact acgccacctc    960
ccctgcagcc gagtgcacgc agcagcctgg cgtgacaagt gggcgacgcc gggggcagg   1020 gagccggggt ccttggccct ggccggggac cccaccgccc accgcgcgga ggacaacttt   1080
tagccggcag cccagaccag cgcggcacct gtctccggag tctccaccgc tcctcccgat   1140
tcatcccagg gaaattctca agaatacgct ctacaaatct acgtgcgcat cattttcacc   1200
tcgcgtcgcg cccggaggag ggaacgagg caaggagcta agcagcgtg cgttcagccc    1260 tggggaggaa aatggaagaa acggagatac ttttagtgaa gcagaataaa ccactgaaca   1320
ggaaaaatga ggaagctgtg agtaccagtg gaaggaacga gccaggaaga gggactggaa   1380
ccatctcaga agccatgccc ctcaggctgg aacttgccct gtctcctcgc agatgagaca   1440
gacgtttaag tacgagaaag ctaatggcgc agattctgct gactgtgtgg ctctcgtctt   1500
aatgcgtttt ccaaccttga acctgagaat gccaga                            1536
```

<210> SEQ ID NO 10
<211> LENGTH: 1630
<212> TYPE: DNA
<213> ORGANISM: Homo sapiens

<400> SEQUENCE: 10

```
aaacagcgat tcttctgcag tgaatcactt ccagaaatga atagccacag ttttttggaa    60
tgaacgttgt gaaatccctc ctttataatg gcaggttttc agttggtggt tttatcagaa   120
tttctcaaga tcaaaacgaa accttctctt taaaaaggaa agaaagtact atcgatacag   180
aaagcaaaag tatttccagt ctcctactga actgtcacgg cagacctctc tgtatctata   240
tttagagctg tatgtccata tatttgcctg aatgtgtgag ttcttggaag tatggattca   300
ttgccaggag ctggtgattt cctaagcaga ggtcgctaac tacaagaaat gttacactcg   360
gacaagtcct gcgcttgggg atcctctgta cgcccgttca ctggtgcagg tcttctgaac   420
aaatgcctcc tgaggatttc tgtgcctgga aaatatctgt aacagactg cttttacacc    480
tacatcagga taccgaagct cagaaaaatt aaatgatttg cccaggatca catagttagt   540
aagcagccca gccagatcct gtgttaactt gttcatccgc ttcctataag aaaacatcca   600
ttcaaggcac atgggcaac aaagaaggac ttagagctgt gtggcccctc gtcagggcag     660
taccagttgc acccatagtc cggcctgaat actcagctta ggactattgt gtccaatgtc   720
ccaaacattt tgaagctaca tcttaaagaa gtgtcctgct cagatgcagt tctccttgtg   780
aaatccgcag gccccaagga aagtgacttt aatccagttt gctcatgcaa gaacagactg   840
gcatttcaca tccaggaaaa caatggattt gtactgttca gcttttgcca tgcaaggagt   900
tcctggtgtg gtttattaat ttacatctca ggctccagct tcactatcaa tcagatttgg   960
aagaaaaaag ttacaaagaa aggcagcttg ctgagaaaca gcggaagcat gacggtacag  1020
actgggtttt gaaatggaga cacattctca tggcttgtgg gctgagagac actgagaaag  1080
gattttgttc ttgaaagatg attgttttaa tgctggagat ggagagtttt gacaatttta  1140
agtgcatgtt ctgtgtgtaa gaaagagtca ttacgttttt tttttctttc agatgttgcc  1200
atgccttaaa attgctgatg attaaaatag aacatcctga gttacagaaa ttcagcccta  1260
gtgtatcctg gcctaaaaat acagaacaat caagttgatt gttggaaatg agaggctagg  1320
cagggttgga acatgctaa tgtttactga gtgaaatctt tccttctcag tagagttgcc    1380
cttgcagctg aaagtcactg aaagactcaa caaaataagc agatcccact tgtctcactc  1440
tgttctccta tgcatgccct ggaaagagaa tgaatgagcc cttttttaatt tatcaactgg  1500
tttttcttcca tctcttttact agtgagccat ggggttttt tgccgttaac tgggtagcca  1560
gtctcttcat ggagacttat tttcaggaaa ctagcctctt gctttatgtg aaaacaagga  1620
cccaactcaa                                                         1630
```

<210> SEQ ID NO 11
<211> LENGTH: 519
<212> TYPE: DNA
<213> ORGANISM: Homo sapiens

<400> SEQUENCE: 11

```
aaacagcgat tcttctgcag tgaatcactt ccagaaatga atagccacag ttttttggaa    60
tgaacgttgt gaaatccctc ctttataatg gcaggttttc agttggtggt tttatcagaa   120
tttctcaaga tcaaaacgaa accttctctt taaaaaggaa agaaagtact atcgatacag   180
aaagcaaaag tatttccagt ctcctactga actgtcacgg cagacctctc tgtatctata   240
tttagagctg tatgtccata tatttgcctg aatgtgtgag ttcttggaag tatggattca   300
ttgccaggag ctggtgattt cctaagcaga ggtcgctaac tacaagaaat gttacactcg   360
gacaagtcct gcgcttgggg atcctctgta cgcccgttca ctggtgcagg tcttctgaac   420
```

-continued

```
aaatgcctcc tgaggatttc tgtgcctgga aaatatctgt taacagactg cttttacacc    480
tacgttgtct tgggtttatt gtaagagagc attatgaag                          519
```

<210> SEQ ID NO 12
<211> LENGTH: 25
<212> TYPE: RNA
<213> ORGANISM: Artificial Sequence
<220> FEATURE:
<223> OTHER INFORMATION: Synthetic siPINT-1 sense

<400> SEQUENCE: 12

```
aagaaauacg cagaacugau uccug                                          25
```

<210> SEQ ID NO 13
<211> LENGTH: 25
<212> TYPE: RNA
<213> ORGANISM: Artificial Sequence
<220> FEATURE:
<223> OTHER INFORMATION: Synthetic siPINT-1 antisense

<400> SEQUENCE: 13

```
caggaaucag uucugcguau uucuu                                          25
```

<210> SEQ ID NO 14
<211> LENGTH: 25
<212> TYPE: RNA
<213> ORGANISM: Artificial Sequence
<220> FEATURE:
<223> OTHER INFORMATION: Synthetic siPINT-2 sense

<400> SEQUENCE: 14

```
ugggauaauu ugccaucugg aguuu                                          25
```

<210> SEQ ID NO 15
<211> LENGTH: 25
<212> TYPE: RNA
<213> ORGANISM: Artificial Sequence
<220> FEATURE:
<223> OTHER INFORMATION: Synthetic siPINT-2 antisense

<400> SEQUENCE: 15

```
aaacuccaga uggcaaauua uccca                                          25
```

<210> SEQ ID NO 16
<211> LENGTH: 25
<212> TYPE: RNA
<213> ORGANISM: Artificial Sequence
<220> FEATURE:
<223> OTHER INFORMATION: Synthetic siPINT-3 sense

<400> SEQUENCE: 16

```
auguaucaaa ugccugguuc uauuu                                          25
```

<210> SEQ ID NO 17
<211> LENGTH: 25
<212> TYPE: RNA
<213> ORGANISM: Artificial Sequence
<220> FEATURE:
<223> OTHER INFORMATION: Synthetic siPINT-3 antisense

<400> SEQUENCE: 17

```
aaauagaacc aggcauuuga uacau                                          25
```

<210> SEQ ID NO 18

```
<211> LENGTH: 25
<212> TYPE: RNA
<213> ORGANISM: Artificial Sequence
<220> FEATURE:
<223> OTHER INFORMATION: Synthetic siPINT-4 sense

<400> SEQUENCE: 18
aaguaggagc cacgaaaugu cauuu                                              25

<210> SEQ ID NO 19
<211> LENGTH: 25
<212> TYPE: RNA
<213> ORGANISM: Artificial Sequence
<220> FEATURE:
<223> OTHER INFORMATION: Synthetic siPINT-4 antisense

<400> SEQUENCE: 19
aaaugacauu ucguggcucc uacuu                                              25

<210> SEQ ID NO 20
<211> LENGTH: 25
<212> TYPE: RNA
<213> ORGANISM: Artificial Sequence
<220> FEATURE:
<223> OTHER INFORMATION: Synthetic siPINT-5 sense

<400> SEQUENCE: 20
agccaggaag agggacugga accau                                              25

<210> SEQ ID NO 21
<211> LENGTH: 25
<212> TYPE: RNA
<213> ORGANISM: Artificial Sequence
<220> FEATURE:
<223> OTHER INFORMATION: Synthetic siPINT-5 antisense

<400> SEQUENCE: 21
augguuccag ucccucuucc uggcu                                              25

<210> SEQ ID NO 22
<211> LENGTH: 20
<212> TYPE: DNA
<213> ORGANISM: Artificial Sequence
<220> FEATURE:
<223> OTHER INFORMATION: Synthetic PINT forward primer

<400> SEQUENCE: 22
aaagcattag gggagcccac                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic PINT reverse primer

<400> SEQUENCE: 23
tgccggctaa aagttgtcct                                                    20
```